(12) United States Patent
Annis

(10) Patent No.: US 6,347,132 B1
(45) Date of Patent: Feb. 12, 2002

(54) HIGH ENERGY X-RAY INSPECTION SYSTEM FOR DETECTING NUCLEAR WEAPONS MATERIALS

(75) Inventor: Martin Annis, Cambridge, MA (US)

(73) Assignee: AnnisTech, Inc., Cambridge, MA (US)

( * ) Notice: Subject to any disclaimer, the term of this patent is extended or adjusted under 35 U.S.C. 154(b) by 0 days.

(21) Appl. No.: 09/320,006

(22) Filed: May 26, 1999

Related U.S. Application Data

(60) Provisional application No. 60/086,742, filed on May 26, 1998, and provisional application No. 60/086,743, filed on May 26, 1998.

(51) Int. Cl.[7] .............................................. G01N 23/201
(52) U.S. Cl. ............................ 378/57; 398/53; 398/88
(58) Field of Search ............................ 378/57, 51, 53, 378/86, 88, 147

(56) References Cited

U.S. PATENT DOCUMENTS

| | | | | |
|---|---|---|---|---|
| 5,044,002 A | * | 8/1991 | Stein ............................ | 378/57 |
| 5,490,218 A | * | 2/1996 | Krug et al. ..................... | 378/57 |
| 5,493,596 A | * | 2/1996 | Annis ............................ | 378/57 |
| 5,524,133 A | * | 6/1996 | Neale et al. .................... | 378/57 |
| 5,917,880 A | * | 6/1999 | Bjorkholm ....................... | 378/57 |

\* cited by examiner

Primary Examiner—Drew Dunn
(74) Attorney, Agent, or Firm—Samuels, Gauthier & Stevens, LLP

(57) ABSTRACT

An x-ray inspection system for automatically detecting nuclear weapons materials generates a high energy x-ray fan beam or a traveling x-ray pencil beam that traverses an object under inspection. An x-ray detector detects x-ray energy that passes through the object and provides a detected signal indicative thereof. The detected signal is processed to detect the presence of an area of very high x-ray attenuation within the object under inspection, which is indicative of nuclear weapons materials. Because of the high atomic number (Z) and high density of nuclear weapons materials Uranium and Plutonium, both of these materials attenuate (i.e., absorb) incident x-rays significantly more than ordinary materials. That is, very high Z materials such as nuclear weapons materials, produce no x-rays outside of their block of material because the x-rays are self absorbed within the very high Z materials. Therefore, these materials can be detected by a transmission detectors, or by combining the readings from transmission and scatter detectors, if a pencil beam system is employed.

14 Claims, 4 Drawing Sheets

HIGH ENERGY X-RAY INSPECTION SYSTEM FOR DETECTING NUCLEAR WEAPONS MATERIALS

CROSS REFERENCE TO RELATED APPLICATIONS

This application claims priority from the provisional applications designated Ser. No. 60/086,742, filed May 26, 1998 and entitled "High Energy X-Ray Inspection System", and Ser. No. 60/086,743, filed May 26, 1998 and entitled "Nuclear Weapons Materials Detection System and Method". Both applications are hereby incorporated by reference.

TECHNICAL FIELD

The invention relates to the field of x-ray inspection systems, and in particular to an x-ray inspection system for automatically detecting nuclear weapons materials within an object under inspection.

BACKGROUND OF THE INVENTION

The detection of contraband (e.g., explosives and drugs) in closed containers is of growing importance worldwide. World events have necessitated tighter screening requirements for the contents of containers placed on aircraft to detect the presence of explosives. In addition, to combat the illegal flow of narcotics across national borders, the contents of containers, such as loaded trucks and vehicles must be inspected to check for the presence of narcotics. High energy x-ray inspection systems remain one of the only technologies capable of inspecting loaded cargo containers and vehicles.

There is also a need to inspect containers for nuclear grade weapons' materials. There is a growing concern that some of these materials may come into possession of terrorists, due to the relatively large volume of nuclear weapons grade materials stored worldwide. Detectors such as Geiger counters and gamma ray detectors are well known for detecting nuclear weapons materials. However, since Uranium does not emit a significant flux of gamma rays, it can not be detected by a gamma ray detector (e.g., a gamma ray detector mounted outside of the truck which contains the contraband). Therefore, there is a need for an x-ray inspection systems capable of automatically detecting the presence of nuclear weapons materials.

SUMMARY OF THE INVENTION

An object of the present invention is to automatically detect nuclear weapons materials using an x-ray inspection system.

Briefly, according to the present invention, an x-ray inspection system generates a high energy x-ray beam that traverses an object under inspection. A detector detects x-ray energy from the object and provides a detected signal indicative thereof. The detected signal is processed to detect the presence of an area of very high x-ray attenuation within the object under inspection, which is indicative of nuclear weapons materials, wherein the x-ray absorption of the nuclear weapons material is much greater than all of the elements of atomic number approximately equal to or lower than iron.

The high energy x-ray beam may be a fan beam or a pencil beam. In a fan beam embodiment, the detector is a transmission detector.

Because of the high atomic number (Z) and high density of nuclear weapons materials Uranium and Plutonium, both of these materials attenuate (i.e., either scatter out of the beam or absorb) incident x-rays significantly more than ordinary materials. In addition, very high Z materials such as nuclear weapons materials (e.g., Uranium and Plutonium), as well as lead, produce no scattered x-rays which are able to penetrate outside of their block of material because the scattered x-rays are self absorbed within the very high Z materials. Therefore, these materials can be detected by a single transmission detector, and, in addition, if the x-ray system forms a pencil beam, by noting that the detectors which monitor the scattered radiation give no signal for the region in question.

Advantageously, the inspection system of the present invention automatically detects the presence of nuclear weapons materials. In addition, the system may also operate to detect other contraband (e.g., drugs and explosives) in addition to nuclear weapons materials.

These and other objects, features and advantages of the present invention will become apparent in light of the following detailed description of preferred embodiments thereof, as illustrated in the accompanying drawings.

DETAILED DESCRIPTION OF THE INVENTION

Figure 1:
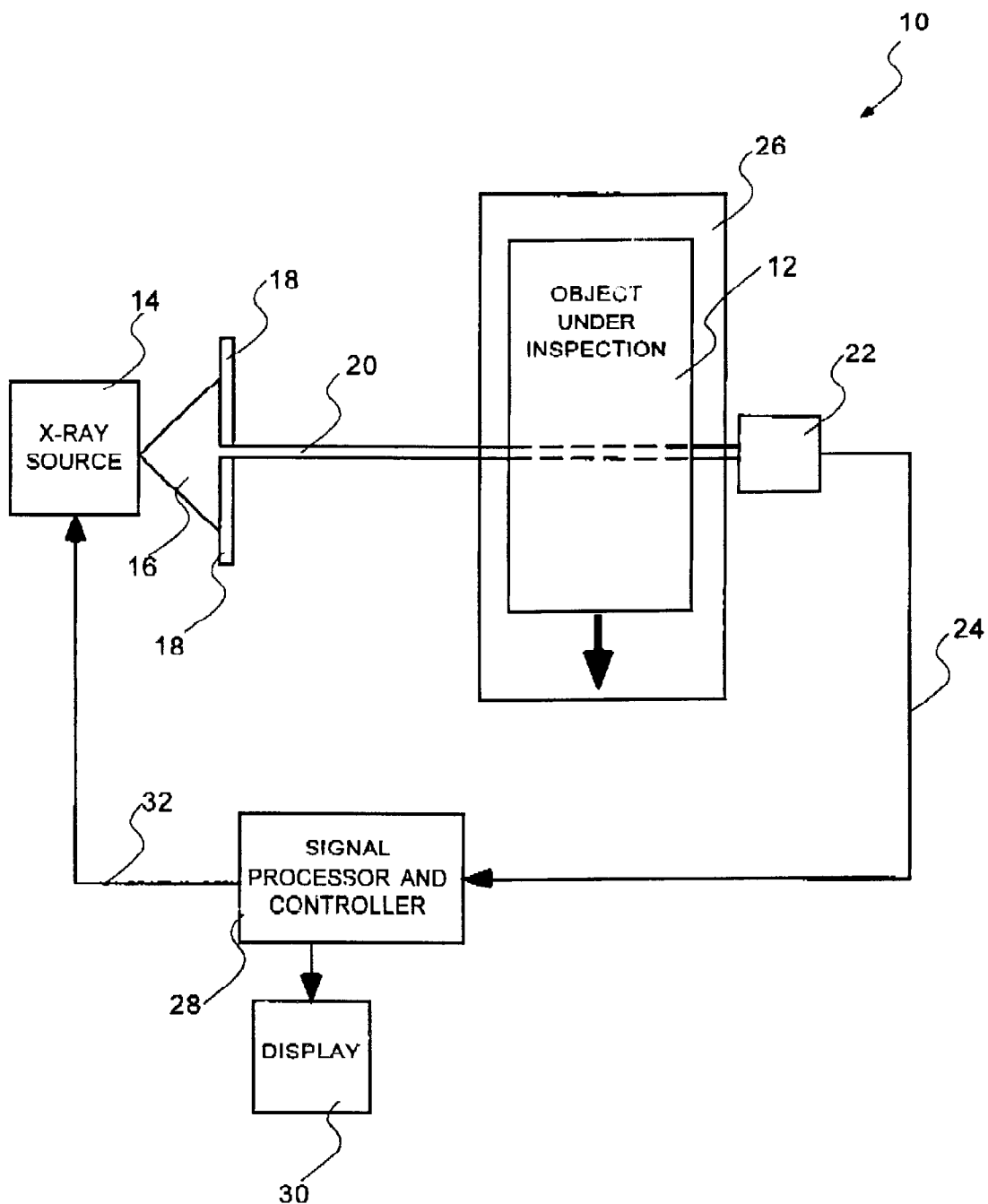
FIG. 1 is a functional block diagram of a high energy X-ray inspection system.

FIG. 1 illustrates a functional block diagram of a high energy X-ray inspection system 10 for inspecting the contents of an object under inspection 12 (e.g., a shipping container), for the case where a fan beam of x-rays is used. The fan beam system 10 includes an x-ray source 14, such as an x-ray tube, a linear accelerator of electrons plus an x-ray target, or a radioactive source such as Cobalt-60. The source 14 provides a cone of x-rays 16 to a collimator 18 which reduces the cone of x-rays 16 to a fan beam of x-rays 20. The fan beam is preferably oriented in a vertical plane as shown.

The fan beam 20 strikes the object under inspection 12, and the x-rays which pass directly through the object are detected by a transmission detector 22 that includes a line of detectors which provide signals on a line 24 indicative of detected x-rays photons. A conveyer system 26 moves the object under inspection transversely (e.g., perpendicularly) through the fan beam of x-rays. If the object under inspection 12 is very large (e.g., a tractor trailer or a shipping container), then rather than using a conveyer, the object may be pulled along perpendicular to the beam of x-rays 20. Alternatively, rather than moving the object under inspection 12, the source 14, the collimator 18 and detectors 22 may move to scan the beam across the stationary object under inspection.

A signal processor and controller 28 receives the detected signals on the line 24, processes the signals, and displays image data on display 30 indicative of the interior of the object under inspection. If the x-ray source 14 is an electronic source, the signal processor and controller 28 provides a control signal on a line 32 to the source. X-ray sources, collimators and transmission detectors (and, if a pencil beam of x-rays is utilized, scatter detectors—not shown) are all well known in the art, and in the interest of brevity those details shall not be repeated herein. The details of detecting nuclear weapons materials shall now be discussed.

Significantly, using a high energy x-ray source enables the x-ray system to detect nuclear weapons materials without additional hardware. Specifically, a high energy x-ray system may operate to detect nuclear weapons by adding an executable detection routine that analyzes the image data to automatically detect the presence of nuclear weapons materials within the object under inspection.

The high energy x-ray source generally has a peak energy of greater than about 450 KeV, and preferably about 1 MeV. Because of the high Z (92 for U, 94 for Pu) and high density ($\rho=19$ g/cm$^3$ for U235 and 19.7 g/cm$^3$ for Pu238) of Uranium and Plutonium, these materials attenuate x-rays emitted by the source more than ordinary materials (with the exception of lead). For example, 310 grams (0.7 pounds) of Uranium in a 1" cube (i.e., 2.5 cm or 47.5 g/cm$^2$ thick) can be detected by a single transmission detector. If a pencil beam is employed, the readings from transmission and scatter detectors are combined.

If the object under inspection is filled with the equivalent of 4" of iron, the attenuation of the iron is about $4\times10^{-3}$ for a 700 kV x-ray photon. On the other hand the attenuation of the U embedded in the iron is about $7\times10^{-5}$ (because of its high Z and $\rho$), or a difference of a factor of about 60. This factor is so great that automatic detection of the nuclear weapons materials can be readily performed. Thus, the system automatically detects nuclear weapons materials by searching for the existence of a small area of the image with a very high x-ray attenuation. In one embodiment, the detection criteria may be set to automatically detect the presence of nuclear weapons material when the x-ray attenuation of an imaged region is at least one standard deviation greater than the surrounding material. If a pencil beam system is employed, the identification is made more positive by noting that the strong local attenuation, in the transmission image, of the suspect region is accompanied by no signal for the same region in the scatter image.

Figure 2:
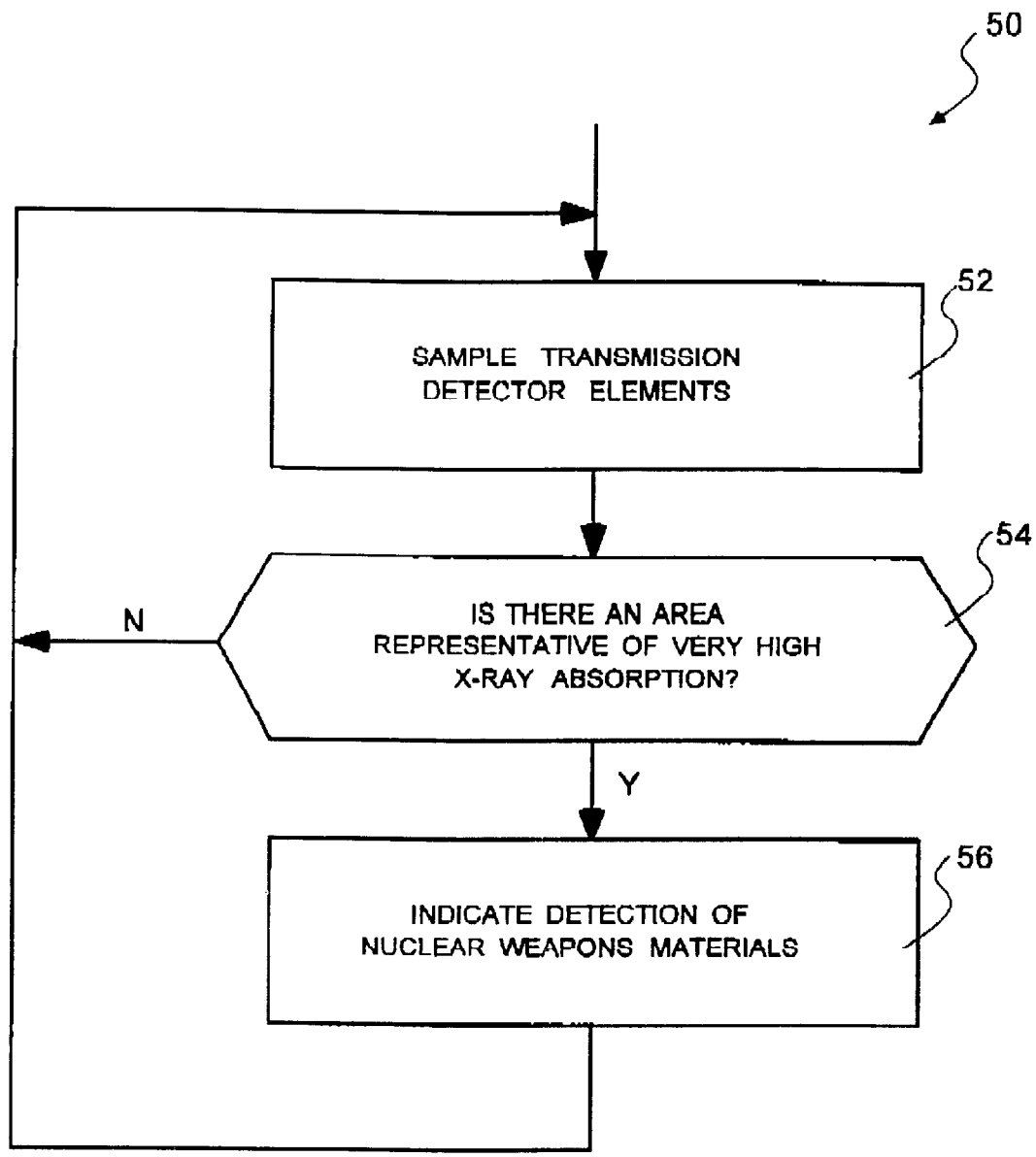
FIG. 2 is a flow chart illustration of an executable routine for detecting nuclear weapons materials.

FIG. 2 is a flow chart illustration of an executable routine 50 for automatically detecting nuclear weapons materials. This routine is preferably executed by the signal processor and controller 28 (FIG. 1). Step 52 is performed to sample each of the individual detector elements of the transmission detector 22 (FIG. 1) as the object under inspection 12 (FIG. 1) is scanned relative to the fan beam 20 (FIG. 1), and digitize and store the sampled values. Test 54 performs a threshold detection on the sampled values to identify any areas of unusually high absorption within the image of the object under inspection. That is, since the nuclear weapons materials absorb x-rays significantly more than any other materials, the magnitude of the sampled signals associated with areas within the object under inspection having nuclear weapons materials will be significantly different than the surrounding areas. Therefore, threshold detection is a suitable automatic detection technique. Alternatively, spatial frequency analysis may also be used to detect large changes in the sampled signal magnitude, which may then be analyzed to determine whether or not the large changes in magnitude are consistent with nuclear weapons materials. In any event, detection of the nuclear weapons materials is automatic. Similarly, the region of high attenuation identified in the transmission image is examined in the scatter image (if the pencil beam system is employed). A negative result in the scatter image reinforces the result from the transmission beam analysis. If nuclear weapons' materials are detected, step 56 provides a warning annunciator that may be displayed on the display, initiates an audio alarm, or provides other suitable warning devices.

Figure 3:
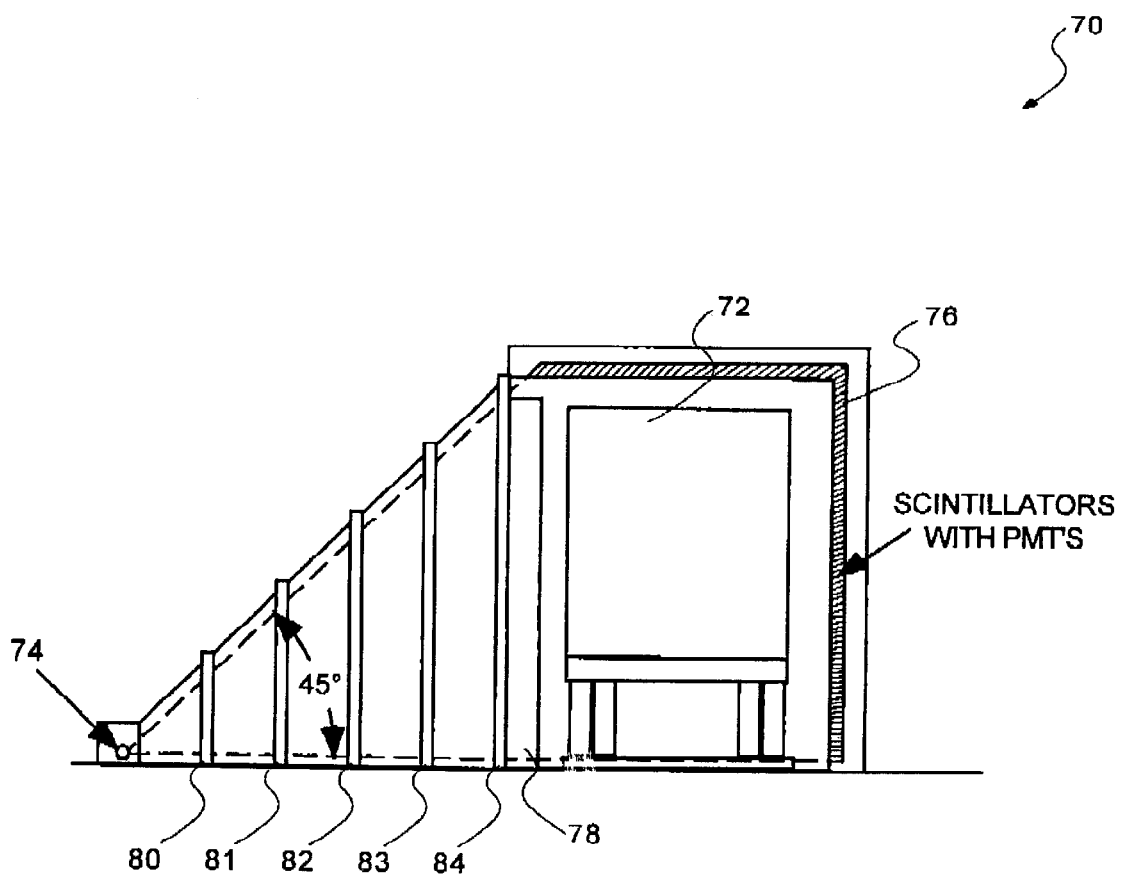
FIG. 3 is a pictorial illustration of a high energy x-ray inspection system having a radioactive x-ray source.

Referring again to FIG. 1, as set forth above the x-ray source may be an electronic x-ray source (e.g., an x-ray tube, an linear accelerator, etc.) or a radioactive source. FIG. 3 illustrates a simplified pictorial illustration of a high energy x-ray inspection system 70 for inspecting shipping containers and tractor trailers 72. The system 70 include a radioactive source containing about 10,000 Curies of Cobalt-60 to achieve the required penetration through the trailer under inspection 72. The source is preferably an off-the-shelf Cobalt-60 source that meets all NRC requirements, including a secure installation of the Cobalt-60 source system with a secure "vault" rendering the Cobalt source inaccessible to unauthorized personnel. The Cobalt-60 radioactive source 74 emits gamma rays of about 1.1–1.2 MeV. These gamma rays are the equivalent in penetrating power of a conventional electronic x-ray source having a peak energy of approximately 2 MeV. Notably, in comparison to a high energy electronic x-ray source, the radioactive source 74 is smaller and requires no power source. In addition, the Cobalt-60 source emits gamma rays in all directions with the same energy. On the other hand, an alternative 2 MeV linear accelerator source emits x-rays of high energy only in a narrow angle of about 22°. This narrow angle requires that the electronic source be mounted about 78 feet away from two sea cargo containers stacked 28' high, one on top of the other. In comparison, the cobalt source can be located about 16' away from the stacked sea cargo containers, using an opening angle of 60°. The source may be packaged in a fully licensed container as supplied e.g., by Neutron Products, Inc. of Dickerson, Md. Notably, the radioactive source allows the system to shoot through the object under inspection at a maximum elevation angle of 60° toward an L-shaped standing array 76 of, for example about 230 sensitive transmission detector elements.

In one embodiment, the radioactive source 74 allows a 60 degree angled fan beam 78 that is defined by a linear series of stationary, vertical, steel, slot "trimmers" 80–83 and a final collimator 84 near the trailer under inspection 72. Each trimmer is a steel column with a single longitudinal slot. The trimmers are aligned with the source 74 and the detector 76. The trimmers 80–83 and the final collimator 84 are conventional, requiring no special machining. They define the fan beam 78, and filter out stray radiation.

Figure 4:
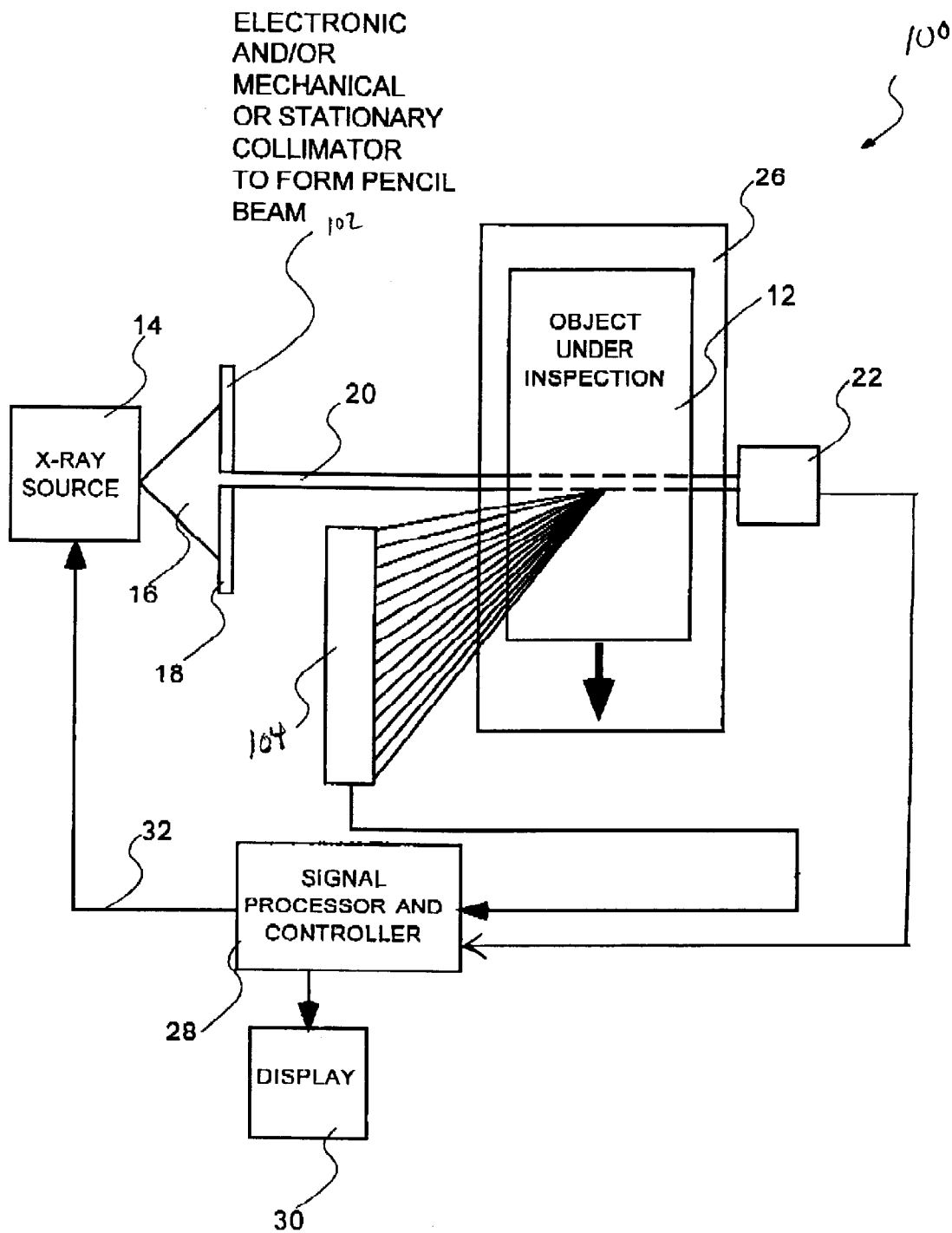
FIG. 4 is a functional block diagram of a high energy X-ray inspection system that employs a pencil beam.

FIG. 4 is a functional block diagram of a high energy X-ray inspection system 100 that employs a pencil beam. This system 100 is substantially the same as the system 10 illustrated in FIG. 1, with the exception that this system employs a collimator 102 that forms a pencil beam, rather than a fan beam. In addition, this system 100 also includes a backscatter detector 104. As set forth above, if a pencil beam system is employed, the identification of nuclear materials is performed by noting areas of strong local attenuation in the transmission image, accompanied by no signal for the same region in the scatter image.

Although the present invention has been discussed in the context of a system employing a transmission detector, one of ordinary skill in the art will recognize that scatter detectors (e.g., backscatter and/or forward scatter) may also be utilized with a pencil beam system, Very high Z materials such as nuclear weapons materials (Uranium and Plutonium) produce no x-rays outside of their block of material because the x-rays are self absorbed within the very high Z materials.

Thus, the automatic detection routine may be configured to identify the "coincidence" of a region of the transmission x-ray image which shows very high absorption, and the identical region of the scatter image which shows no x-rays, and the presence of both indicates the presence of very high Z material such as nuclear weapons materials. In addition, although a Cobalt-60 source has been discussed in detail, one of ordinary skill will recognize that other radioactive sources may also be used.

Although the present invention has been shown and described with respect to several preferred embodiments thereof, various changes, omissions and additions to the form and detail thereof, may be made therein, without departing from the spirit and scope of the invention.

What is claimed is:

1. A method of detecting nuclear weapons materials with an x-ray inspection system, the method comprising the steps of:
   providing a high energy x-ray fan beam that traverses an object under inspection;
   transmission detecting x-ray energy that passes through the object under inspection, and providing detected signals indicative thereof; and
   processing said detected signals to detect the presence of an area of very high x-ray attenuation which is indicative of nuclear weapons materials, wherein the x-ray attenuation of the nuclear weapons material is at least one standard deviation greater than the surrounding material.

2. The method of claim 1, wherein said high energy x-ray fan beam has a peak energy of at least about 450 KeV.

3. The method of claim 2, wherein said step of providing a high energy x-ray fan beam that traverses an object under inspection, comprises the steps of:
   providing a radioactive source that generates a cone of x-rays; and
   collimating said cone of x-rays to provide said fan beam.

4. The method of claim 2, wherein said step of providing a high energy x-ray fan beam that traverses an object under inspection, comprises the steps of:
   providing an electronic x-ray source that generates a cone of x-rays; and
   collimating said cone of x-rays to provide said fan beam.

5. The method of claim 1, wherein said step of processing includes the step of comparing the magnitude of said detected signals to determine the presence of an area of very high x-ray attenuation which is indicative of nuclear weapons materials.

6. An x-ray inspection system for inspecting an object to detect nuclear weapons materials, the system comprising:
   means for providing a high energy x-ray fan beam that traverses the object;
   a transmission detector that detects x-ray energy that passes through the object under inspection using a plurality of detector elements which collectively define said transmission detector, and provides detected signals indicative thereof; and
   means for processing said detected signals to detect the presence of an area of very high x-ray attenuation which is indicative of nuclear weapons materials, wherein the x-ray absorption of the nuclear weapons' material is at least one standard deviation greater than the surrounding material.

7. The system of claim 6, wherein said means for providing generates said high energy x-ray fan beam having a peak energy level of at least about 450 KeV.

8. The system of claim 7, wherein said means for providing comprises:
   a radioactive source that generates a cone of x-rays; and
   a collimator that receives said cone of x-rays and provides said fan beam.

9. The system of claim 7, wherein said means for providing comprises:
   an electronic x-ray source that generates a cone of x-rays; and
   a collimator that receives said cone of x-rays and provides said fan beam.

10. The system of claim 9, wherein said electronic x-ray source comprises a linear accelerator.

11. An x-ray inspection system for inspecting an object to detect nuclear weapons materials, the system comprising:
    an x-ray source that provides a high energy x-ray fan beam that traverses an object under inspection;
    a detector that detects x-ray energy from the object under inspection and provides a detected signal indicative thereof; and
    a signal processor that processes said detected signal to detect the presence of an area of very high x-ray attenuation which is indicative of nuclear weapons materials, wherein the x-ray absorption of the nuclear weapons material is at least an order of magnitude greater than lead.

12. The system of claim 11, wherein said signal processor comprises means for processing said detected signal to determine if the spatial content of said transmission detected signal includes an area indicative of the presence of a material attenuating the x-rays by one standard deviation greater than the surrounding material.

13. The system of claim 12, wherein said detector comprises a transmission detector.

14. A method of detecting nuclear weapons materials with an x-ray inspection system, the method comprising the steps of:
    providing a high energy x-ray pencil beam that traverses an object under inspection;
    transmission detecting x-ray energy that passes through the object under inspection, and providing transmission detected signals indicative thereof;
    scatter detecting x-ray energy that is emitted by the object under inspection, and providing scatter detected signals indicative thereof;
    processing said transmission detected signals to detect the presence of an area of very high x-ray attenuation which is indicative of nuclear weapons materials, wherein the x-ray attenuation of the nuclear weapons material is at least one standard deviation greater than the surrounding material;
    processing said scatter detected signals to detect the absence of a scatter signal in the area of very high x-ray attenuation as further indication of nuclear weapons' material.

* * * * *